US012734148B2

(12) United States Patent
Kuo et al.

(10) Patent No.: US 12,734,148 B2
(45) Date of Patent: Sep. 15, 2026

(54) **METHOD FOR TREATING DIABETES BY USING *ANTRODIA CAMPHORATA* COMPOUND**

(71) Applicant: Lantyng Biotechnology Corp., Taipei City (TW)

(72) Inventors: Mao-tien Kuo, Taipei City (TW); Yin-yu Kuo, Taipei City (TW); Hui-ling Tseng, Taipei City (TW); Tai-lin Tseng, Taipei City (TW); Wan-ping Tseng, Taipei City (TW); Yi-ling Ye, Taipei City (TW); Li-shian Shi, Taipei City (TW); Ya-hong Lin, Taipei City (TW)

(73) Assignee: LANTYNG BIOTECHNOLOGY CORP., Taipei City (TW)

( * ) Notice: Subject to any disclaimer, the term of this patent is extended or adjusted under 35 U.S.C. 154(b) by 366 days.

(21) Appl. No.: 18/421,544

(22) Filed: Jan. 24, 2024

(65) Prior Publication Data

US 2025/0041264 A1 Feb. 6, 2025

(30) Foreign Application Priority Data

Aug. 2, 2023 (TW) ................................ 112129165

(51) Int. Cl.

| | |
|---|---|
| ***A61K 31/357*** | (2006.01) |
| ***A61K 36/07*** | (2006.01) |
| ***A61P 3/06*** | (2006.01) |
| ***A61P 3/10*** | (2006.01) |

(52) U.S. Cl.

CPC ............ *A61K 31/357* (2013.01); *A61K 36/07* (2013.01); *A61P 3/06* (2018.01); *A61P 3/10* (2018.01)

(58) Field of Classification Search

CPC ......... A61K 31/357; A61K 36/07; A61P 3/06; A61P 3/10

See application file for complete search history.

(56) References Cited

FOREIGN PATENT DOCUMENTS

| | | | |
|---|---|---|---|
| CN | 104887661 | A | 9/2015 |
| CN | 107365293 | A | 11/2017 |
| TW | I527583 | B | 4/2016 |
| TW | I626053 | B | 6/2018 |

OTHER PUBLICATIONS

Wang, C.-L. et al. Aqueous extract of Antrodia cinnamomea reduced high-fat diet-induced obesity in mice and suppressed adipogenesis in 3T3-L1 cells. Journal of Functional Foods 2017, 35, 185-196. (Year: 2017).*

Cherng, I. H., and Chiang, H. C. 1995. "Three new triterpenoids from Antrodia cinnamomea". J. Nat. Prod. 58:365-371.

Chen, C. H., and Yang, S. W. 1995. "New steroid acids from Antrodia cinnamomea,—a fungus parasitic on Cinnamomum micranthum". J. Nat. Prod. 58:1655-1661.

Chiang, H. C., Wu, D. P., Cherng, I. W., and Ueng, C. H. 1995. "A sesquiterpene lactone, phenyl and biphenyl compounds from Antrodia cinnamomea". Phytochemistry. 39:613-616.

Cherng, I. H., Wu, D. P., and Chiang, H. C. 1996. "Triteroenoids from Antrodia cinnamomea". Phytochemistry. 41:263-267.

Yang, S. W., Shen, Y. C., and Chen, C. H. 1996. "Steroids and triterpenoids of Antrodia cinnamomea—a fungus parasitic on Cinnamomum micranthum". Phytochemistry. 41:1389-1392.

* cited by examiner

*Primary Examiner* — Jeffrey H Murray
*Assistant Examiner* — Kristen W Romero
(74) *Attorney, Agent, or Firm* — WPAT, PC

(57) ABSTRACT

The object of the present disclosure is to provide a method for treating diabetes by using an *Antrodia camphorata* compound, wherein the *Antrodia camphorata* compound is shown in the following formula 1:

formula 1 or the pharmacologically acceptable salts of the formula 1.

5 Claims, 5 Drawing Sheets

METHOD FOR TREATING DIABETES BY USING *ANTRODIA CAMPHORATA* COMPOUND

CROSS-REFERENCE TO RELATED APPLICATION

This application claims priority of Taiwan patent application No. 112129165, filed on Aug. 2, 2023, the content of which is incorporated herein in its entirety by reference.

BACKGROUND OF THE INVENTION

1. Field of the Invention

The present invention relates to a method for treating diabetes, especially a method for treating diabetes by using an *Antrodia camphorata* compound.

2. The Prior Art

*Antrodia camphorata*, also known as *Antrodia cinnamomea, Taiwanofungus camphoratus* or red *Antrodia*, etc., belongs to the perennial mushrooms of the order Aphyllophorales and the family Polyporaceae, and is a unique fungus in Taiwan. It only grows on the inner wall of the hollow decaying heartwood of Taiwan's conservation tree species *Cinnamoum kanehirai* Hay. Due to the extremely rare distribution of camphor trees and man-made illegal logging, the number of wild *Antrodia camphorata* that can grow parasitic on it is even rarer. Because its fruiting bodies grow very slowly, and the growth period is only between June and October, the price is very expensive.

Among many components of *Antrodia camphorata*, the most studied are triterpenoids. Triterpenoids are a general term for hexagonal or pentagonal natural compounds combined by 30 carbon elements. The bitter taste of *Antrodia camphorata* mainly comes from triterpenoids. In 1995, Cherng et al. found that the extract of *Antrodia camphorata* fruiting bodies contained three new triterpenoids with ergostane as the skeleton: antcin A, antcin B and antcin C (Cherng, I. H., and Chiang, H. C. 1995. Three new triterpenoids from *Antrodia cinnamomea*. J. Nat. Prod. 58:365-371). Chen et al. found three triterpenoids, zhankuic acid A, zhankuic acid B, and zhankuic acid C, after extracting the fruiting bodies of *Antrodia camphorata* with ethanol (Chen, C. H., and Yang, S. W. 1995. New steroid acids from *Antrodia cinnamomea*, a fungus parasitic on *Cinnamomum micranthum*. J. Nat. Prod. 58:1655-1661). In addition, in 1995, Chiang et al. also discovered three other new triterpenoids, which were sesquiterpene lactone and two biphenol derivatives, namely antrocin, 4,7-dimethoxy-5-methy-1,3-benzodioxole, and 2,2',5,5'-teramethoxy-3,4,3',4'-bimethylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39:613-616). In 1996, Cherng et al. discovered four new triterpenoids with the same analysis method: antcin E, antcin F, methyl antcinate G, and methyl antcinate H (Cherng, I. H., Wu, D. P., and Chiang, H. C. 1996. Triteroenoids from *Antrodia cinnamomea*. Phytochemistry. 41:263-267). Yang et al. discovered two new compounds zhankuic acid D and zhankuic acid E with ergosterane as the backbone, and three new compounds with lanostane as the backbone: 15α-acetyldehydrosulphurenic acid, dehydroeburicoic acid and dehydrasulphurenic acid (Yang, S. W., Shen, Y. C., and Chen, C. H. 1996. Steroids and triterpenoids of *Antrodia cinnamomea-a* fungus parasitic on *Cinnamomum micranthum*. Phytochemistry. 41:1389-1392).

Diabetes belongs to endocrine and metabolic chronic diseases, is the absolute or relative deficiency of insulin secretion and causes sugar, fat and protein metabolic disorders, and is clinically divided into two types, type 1 and type 2. Type 1 is insulin-dependent (IDDM), most of which are caused by autoimmunity. Patients cannot secrete insulin due to damage to pancreatic β cells, resulting in absolute insulin deficiency. Type 2 is non-insulin-dependent (NIDDM). The islet β cells of patients still have the function of secreting insulin, but because the insulin receptors of the target cells (corresponding cells) are resistant or insensitive to insulin, insulin is not released when needed. The binding force between receptor and insulin decreases. Although the amount of insulin is normal, it cannot meet the needs of maintaining normal metabolism, resulting in elevated blood sugar and increased urine sugar. This situation is called relative insulin deficiency.

Taking the invention patent previously filed by the Applicant as an example, such as the invention patent of the Republic of China patent number 1527583 "Medicinal composition for promoting wound healing, and use thereof", the invention patent of the Republic of China patent number 1626053 "Use of *Antrodia camphorata* compound for manufacture of composition for promoting hair growth", the invention patent of the People's Republic of China patent number CN104887661B "Medicinal composition for promoting wound healing, and use thereof" and the People's Republic of China patent application number CN201610313277.9 "Application of *Antrodia camphorata* extract and *Antrodia camphorata* compound in preparation of composition for promoting hair growth", they have disclosed the compound 4,7-dimethoxy-5-methyl-1,3-benzodioxole (SY1 for short), which has the effect of promoting wound healing and hair growth, and has the potential to develop related medical compositions. However, whether this compound has other medical uses remains to be studied. So far, there is no literature disclosing that this compound can be used to reduce blood sugar, blood lipids and other related uses to improve type 2 diabetes.

SUMMARY OF THE INVENTION

Accordingly, the inventors have studied the *Antrodia camphorata* compound quite extensively. After painstaking research and repeated tests, we gradually find out the relevant uses of specific aspects. For example, the relevant uses disclosed in the present application are reducing blood sugar, blood lipids, etc. to improve type 2 diabetes.

A primary objective of the present invention is to provide a method for treating diabetes, comprising administering to a subject in need thereof a pharmaceutical composition comprising an effective amount of an *Antrodia camphorata* compound, wherein the *Antrodia camphorata* compound is shown in the following formula 1:

formula 1

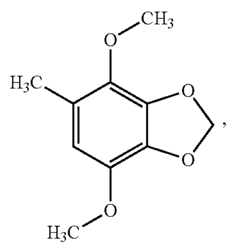

or pharmacologically acceptable salts of the formula 1.

Preferably, the pharmaceutical composition further comprises a pharmaceutically acceptable carrier.

Preferably, the diabetes is type 2 diabetes.

Preferably, the diabetes is treated by lowering blood sugar in the subject in need thereof.

Preferably, the diabetes is treated by reducing blood lipids in the subject in need thereof.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
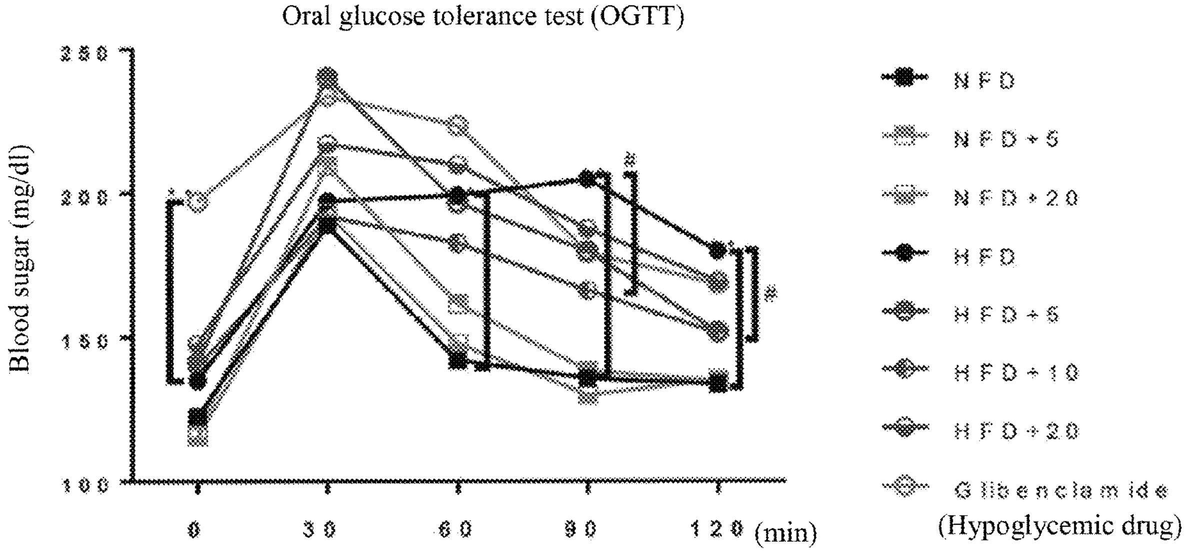
FIGS. 1 and 2 show the results of the oral glucose tolerance test (OGTT).

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Preparation of *Antrodia camphorata* Extract SY-C and Compound SY-1

The *Antrodia camphorata* mycelium, fruiting bodies or a mixture of the two were taken, extracted with water or an organic solvent, so as to obtain *Antrodia camphorata* water extract or organic solvent extract. First, 1.0 kg of *Antrodia camphorata*, its mycelium, fruiting body or the mixture of the two were taken, and extracted twice with 10 times the amount of alcohol, followed by combination and concentration to obtain about 230 g of crude extract. The above-mentioned crude extract was further subjected to three partition extraction methods with dichloromethane/water (1:1) solution, and it was divided into about 102.6 g of dichloromethane layer and about 127.4 g of water layer. 6.0 g of the dichloromethane layer was taken and silica gel column chromatography was used to separate into four fractions (i.e., LT-E-D-1, LT-E-D-2, LT-E-D-3, and LT-E-D-4). The acquisition of the above four fractions is as follows. After extracting with n-hexane/dichloromethane (1:4) and dichloromethane eluent respectively, the obtained fractions were combined to form LT-E-D-1. After eluting with methanol/dichloromethane (5:95) eluent, the fraction obtained in the first half is LT-E-D-2, the fraction obtained in the second half is LT-E-D-3, and LT-E-D-4 was obtained by eluting with methanol. The LT-E-D-1 fraction was recycled as the *Antrodia camphorata* extract SY-C.

In order to further purify the effective components of *Antrodia camphorata* extract SY-C, the LT-E-D-1 layer was taken out, and then can be separated and purified by silica gel column chromatography or preparative high performance liquid chromatography, thus purifying the compound 4,7-dimethoxy-5-methyl-1,3-benzodioxole having the following formula 1 (i.e., SY-1):

formula 1

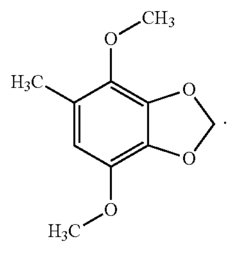

Organic solvents may include but not limited to alcohols (e.g. methanol, ethanol or propanol), esters (e.g. ethyl acetate), alkanes (e.g. hexane) or haloalkanes (e.g. methyl chloride and ethyl chloride). The preferred one is alcohols, and the more preferred one is ethanol. The weight ratio of the organic solvent to the mycelium, the fruiting body or the mixture of the two can be 15:1-5:1, preferably 12:1-8:1, but not limited thereto. In addition, the ratio of dichloromethane/water solution can be between 2:1-1:2, and it is not limited to this.

Regarding the extraction of 4,7-dimethoxy-5-methyl-1,3-benzodioxole, it is described in Tu S H., J Agric FoodChem. 2012 Apr. 11; 60(14):3612-8.

In previous relevant studies, whether it is the *Antrodia camphorata* extract or the purified SY-1 compound, it mainly focuses on its anti-tumor effect, and there is no research on the treatment of diabetes. The present invention uses the compound SY-1 purified from *Antrodia camphorata* and the salts thereof to carry out experiments, and it is found and confirmed that both of them have the effect of promoting insulin secretion, which belongs to a novel use that has never been seen before.

Animal Model of Type 2 Diabetic Mice

This experiment uses four-week-old male mice C57BL/6JNarl from National Laboratory Animal Center (Taipei, Taiwan), and they were bred with 12 hours of light/dark cycle under the environment of 23° C.±2° C.

Mice were adapted to feed water and food arbitrarily every week, and after one week, they were fed in groups from the commercial feed 1320 (containing 11% fat) purchased from EJOY2 CORP. (New Taipei City, Taiwan) and D12451 (containing 45% high-fat feed) purchased from MEDGENE CO., LTD. (Taichung, Taiwan), induced for 12 weeks.

The amount of water and the amount of feed were calculated every week and the litter urine volume was observed every week to monitor whether the status of the mice changes (data not shown), so as to know whether the mice have the diabetic model.

During the experiment, the body weight of the mice and the fasting blood sugar value were measured every week and their changes were recorded. The mean±3SD of fasting blood sugar in mice was calculated. If the fasting blood sugar value exceeds the mean±3SD of the normal diet group, tube feeding administration of the drug (i.e., either SY1 or Glibenclamide) would be initiated once daily started for a duration of 4 weeks, and blood sugar tolerance would be tested by tail vein blood collection in the last week of the experiment.

On the last day of the experiment, all animals (except for unplanned deaths) were fasted for 20 hours at the National Laboratory Animal Center and euthanized with pure carbon dioxide, followed by necropsy, organ weight (liver) and gross examination, including evaluation of liver and pancreas. Most lesions of animals were recorded at the time of final sacrifice, including scheduled euthanasia and unscheduled deaths.

Experimental Design and Methods (AST). ALT mainly exists in liver cells, while AST mainly exists in liver, myocardium, muscle, and also in red blood cells. When these cells are necrotic and destroyed due to various reasons, the ALT and AST in the cells would be released into the blood, so when hepatitis, myocardial infarction, muscle inflammation or hemolysis, the AST value may increase. Blood test to test the rise of these enzymes can infer the degree of cell damage. Similarly, the increase of ALT value can be described to be caused by liver inflammation, and the liver function can be evaluated by detecting the above two enzymes.

Figure 3:
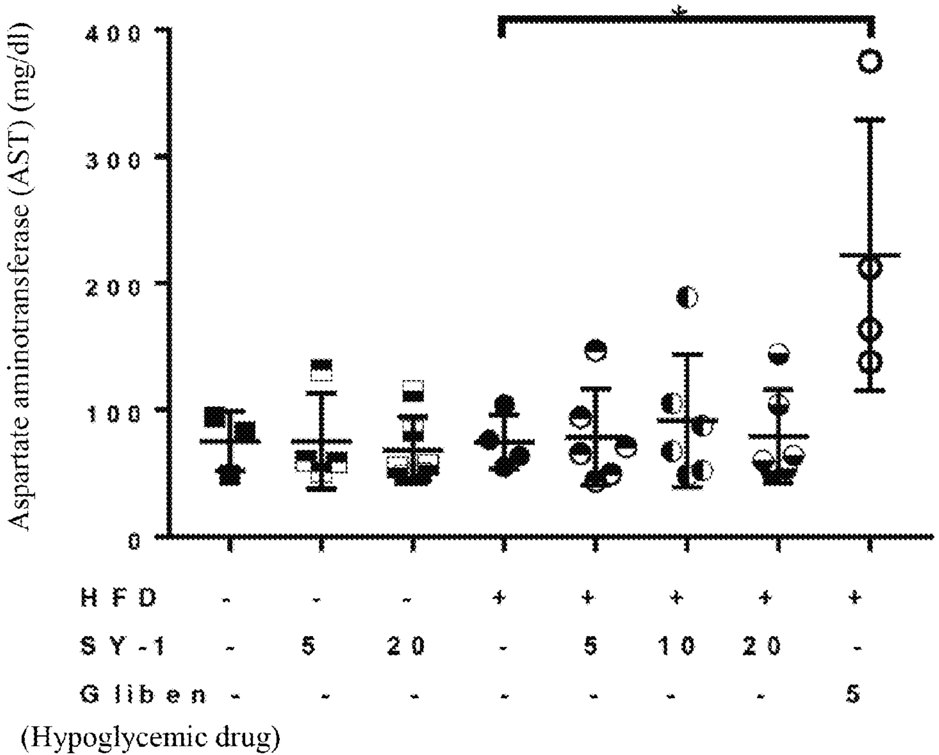
FIG. 3 shows the results of biochemical detection of glutamate oxaloacetate transaminase (AST).
Figure 4:
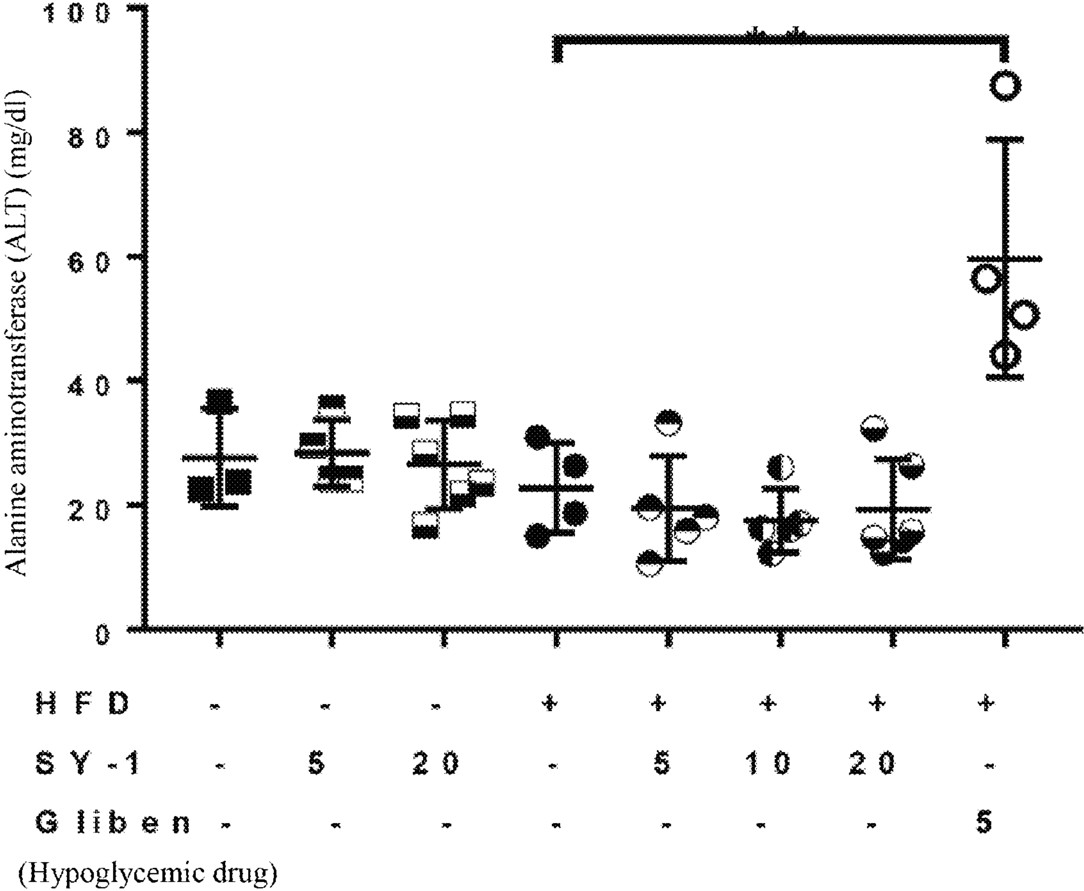
FIG. 4 shows the results of biochemical detection of alanine aminotransferase (ALT).
Figure 5:
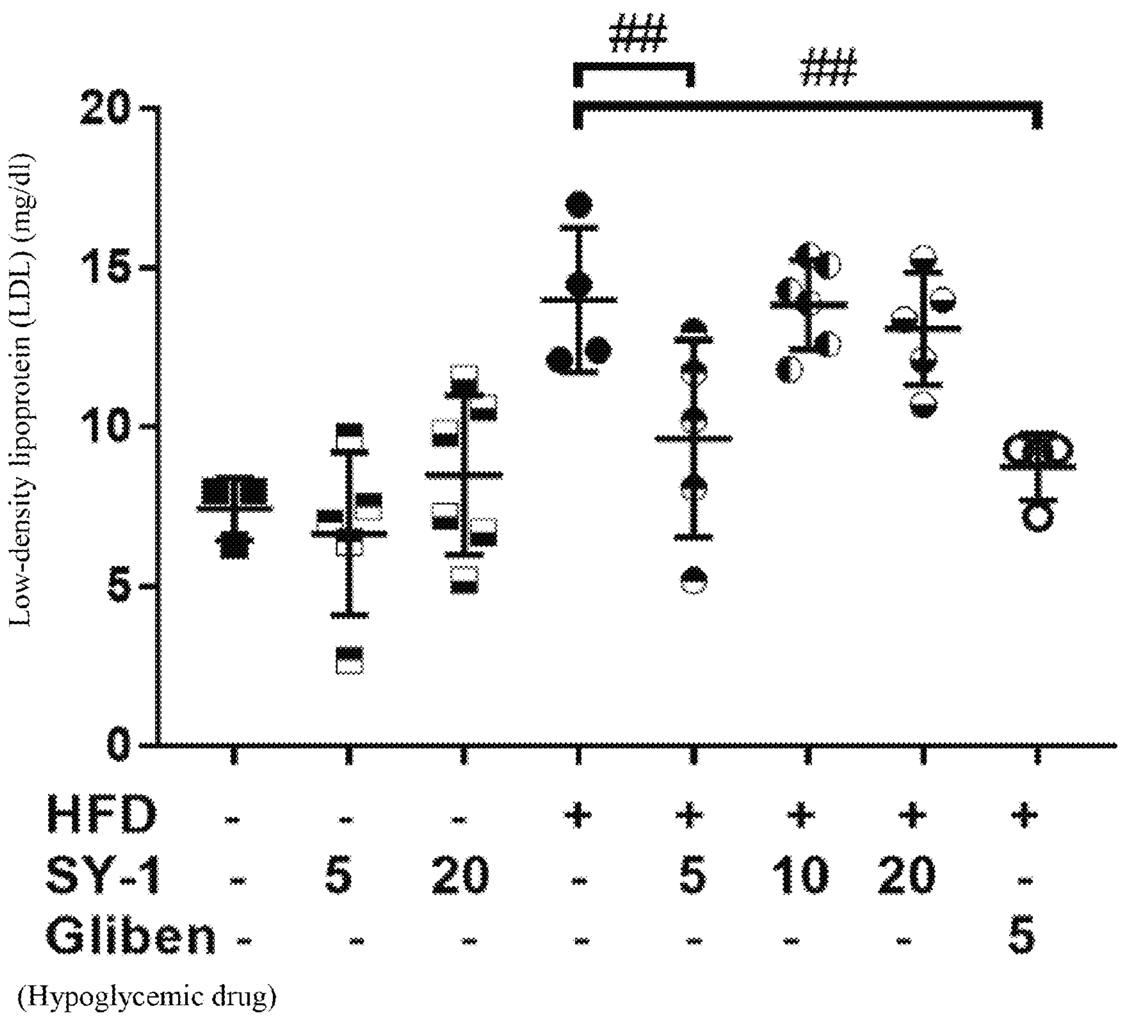
FIG. 5 shows the results of biochemical detection of low-density lipoprotein (LDL).

In this experiment, Hitachi 7080 blood biochemical analyzer and related reagents were used, and the National Laboratory Animal Center was commissioned to detect. The results are shown in FIGS. 3-4, which respectively show the biochemical analysis results of AST and ALT in blood. In terms of liver function in the later stage of treatment, there was little difference among the groups, but the liver function index of the Western medicine group increased and reached a significant difference. Long-term use of the Western medicine may cause slight damage to the liver, but this phenomenon was not seen in the SY1 group during the same treatment period.

TABLE 1

| Each experimental group and dosing treatment conditions | | | | | | | | |
|---|---|---|---|---|---|---|---|---|
| | A | B | C | D | E | F | G | H |
| HFD | − | − | − | + | + | + | + | + |
| DRUG | − | + SY1(5 mg/kg) | + SY1 (20 mg/kg) | − | + SY1 (5 mg/kg) | + SY1 (10 mg/kg) | + SY1 (20 mg/kg) | + Glibenclamide (5 mg/kg) |

Glucose Tolerance Test (Final Week)

Figure 2:
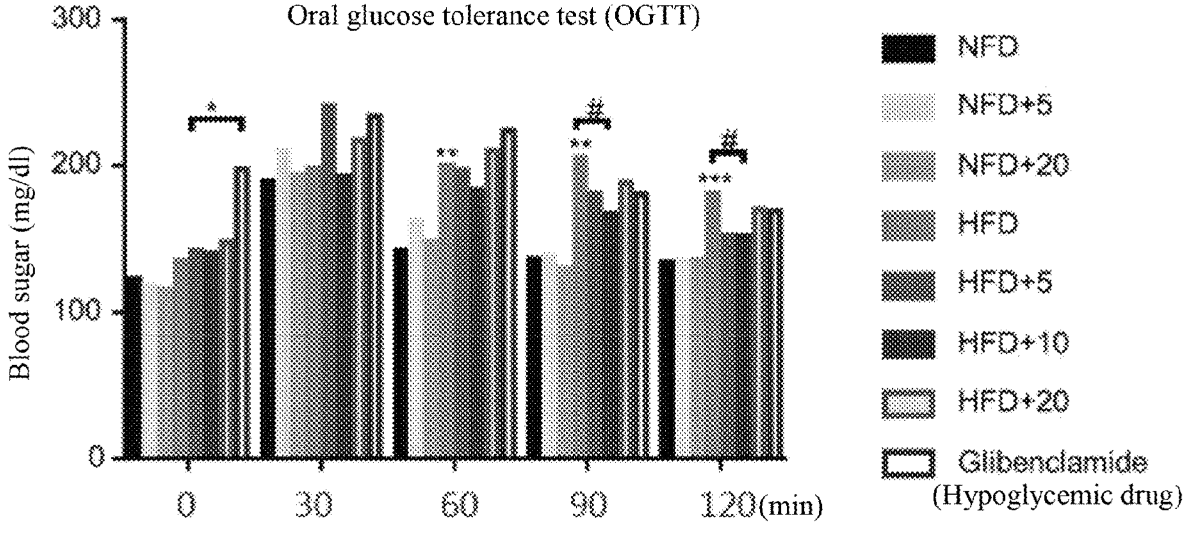

Referring to FIGS. 1-2, they show the test results of oral glucose tolerance test (OGTT), respectively. Each group shown in FIGS. 1-2 corresponds to the conditions shown in Table 1. Group A (NFD), Group B (NFD+5), Group C (NFD+20), Group D (HFD), Group E (HFD+5), Group F (HFD+10), Group G (HFD+20), Group H (Glibenclamide). NFD refers to normal fat diet, HFD refers to high fat diet, and Glibenclamide is an oral hypoglycemic drug that belongs to type 2 (non-insulin dependent) diabetic patients.

The results show that according to the results of the oral glucose tolerance test (OGTT) at the 16th week, it can be seen that the group that added the hypoglycemic drug Glibenclamide had a higher fasting blood sugar increase than any other group when no sugar water was fed. It can be seen that after 4 weeks of drug treatment, the effect of this drug on lowering blood sugar is worse than that of SY1 in the later stage of treatment.

In the part of feeding SY1, 30 minutes after feeding sugar water, SY1 has obvious effect on lowering blood sugar in the low-dose and middle-dose groups of HFD+5 and HFD+10. In the HFD+5 group, it can be seen that the hypoglycemic effect is equivalent to that of the HFD+10 group (n=6, the average blood sugar at 120 minutes of HFD+5 and HFD+10 is 155.83 and 155.33 respectively), and the effect is more obvious than the high-dose HFD+20 and hypoglycemic drug Glibenclamide group.

ALT and AST Biochemical Analysis in Blood

Two aminotransferases in the blood, including alanine aminotransferase (ALT) and aspartate aminotransferase Low-Density Lipoprotein (LDL) Detection Low-density lipoprotein (LDL) is one of the five major groups of lipoproteins. LDL is a large spherical macromolecule that transports hydrophobic molecules (lipids and cholesterol) throughout the body through the aqueous environment of the blood. Low-density lipoproteins (LDLs) deliver fat molecules to cells, and if they become oxidized within the artery walls, atherosclerosis may develop. Since oxidized LDL is more easily retained by proteoglycans, there is a risk of cardiovascular disease when it invades the endothelium. Therefore, high levels of LDL are associated with arterial inflammation, leading to cardiovascular diseases (CVD) such as atherosclerosis, ischemic stroke, and myocardial infarction.

In the part of LDL test results, the effect of HFD+5 group on lowering LDL is not much different from that of the Western medicine group, and is also better than HFD+10. It has been proved again that the HFD+5 group is the best dose in terms of lowering blood sugar or lowering LDL.

The method for treating diabetes by using an *Antrodia camphorata* compound provided by the present invention really has values for industrial use.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating diabetes, comprising administering to a subject in need thereof a pharmaceutical composition comprising an effective amount of an *Antrodia camphorata* compound, wherein the *Antrodia camphorata* compound is shown in the following formula 1:

formula 1

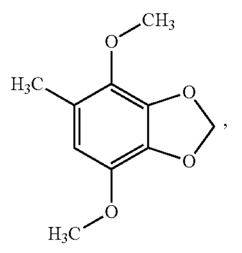

or a pharmacologically acceptable salt of the compound of formula 1.

2. The method according to claim 1, wherein the pharmaceutical composition further comprises a pharmaceutically acceptable carrier.

3. The method according to claim 1, wherein the diabetes is type 2 diabetes.

4. The method according to claim 3, wherein the diabetes is treated by lowering blood sugar in the subject in need thereof.

5. The method according to claim 3, wherein the diabetes is treated by reducing blood lipids in the subject in need thereof.

* * * * *